US 6,964,187 B2
Nov. 15, 2005

(54) VACUUM SENSOR

(75) Inventor: John E. Pillion, Brookline, NH (US)

(73) Assignee: Mykrolis Corporation, Billerica, MA (US)

( * ) Notice: Subject to any disclaimer, the term of this patent is extended or adjusted under 35 U.S.C. 154(b) by 0 days.

(21) Appl. No.: 10/468,413

(22) PCT Filed: Jan. 31, 2002

(86) PCT No.: PCT/US02/02923

§ 371 (c)(1),
(2), (4) Date: Aug. 19, 2003

(87) PCT Pub. No.: WO02/075281

PCT Pub. Date: Sep. 26, 2002

(65) Prior Publication Data

US 2004/0079136 A1 Apr. 29, 2004

Related U.S. Application Data

(60) Provisional application No. 60/270,117, filed on Feb. 20, 2001.

(51) Int. Cl.[7] .................. G01N 21/00; G01D 18/00
(52) U.S. Cl. ................ 73/1.07; 73/23.2; 702/87; 702/100
(58) Field of Search ................ 73/32.2, 1.07; 702/87, 100; 137/565.23

(56) References Cited

U.S. PATENT DOCUMENTS 3,229,500 A * 1/1966 Kraus .................. 73/31.04
3,783,678 A * 1/1974 Das et al. .............. 73/1.58
3,968,675 A * 7/1976 Briggs .................. 73/1.06
4,008,388 A * 2/1977 McLafferty et al. ......... 702/27
4,383,431 A * 5/1983 Gelernt .................. 73/1.62
5,142,143 A * 8/1992 Fite et al. .............. 250/288
5,287,775 A * 2/1994 Moore .................. 81/121.1
5,817,921 A * 10/1998 Tom et al. .............. 73/24.01
6,146,492 A * 11/2000 Cho et al. .............. 156/345.24
6,155,097 A * 12/2000 Arnold .................. 73/23.35
6,156,578 A * 12/2000 Tom .................... 436/149
6,223,770 B1 * 5/2001 Snow .................... 137/565.23
6,257,048 B1 * 7/2001 Hietala et al. ............ 73/24.01
6,279,503 B1 * 8/2001 Choi et al. .............. 118/715
6,286,362 B1 * 9/2001 Coffman et al. ........... 73/40.7
6,468,814 B1 * 10/2002 Frees et al. .............. 438/14

FOREIGN PATENT DOCUMENTS

| EP | 370150 A | * | 5/1990 |
| JP | 2000-97910 A | * | 4/2000 |
| WO | WO 02/075281 | | 9/2002 |

* cited by examiner

Primary Examiner—Michael Cygan
(74) Attorney, Agent, or Firm—Timothy J. King; John E. Pillion

(57) ABSTRACT

An apparatus and method for measuring the vapor or gas content of a vacuum chamber (1) by a vapor sensor (21) located in the fore-line of a vacuum system is provide. The gas or vapor content is determined by first providing a zero condition for the sensor using the vacuum pump (25) and them referencing the sensor response to the chamber gas during the evacuation cycle.

6 Claims, 5 Drawing Sheets

VACUUM SENSOR

This application claims the benefit of U.S. Provisional Application No. 60/270,117, filed Feb. 20, 2001.

FIELD OF INVENTION

This invention relates in part to a method and apparatus for measuring the concentration of a gas or vapor in a vacuum chamber. More particularly, this invention relates to an apparatus and method for sensing and determining the gas or vapor concentration in a vacuum chamber during the evacuation process. The invention also relates to a method for interpreting the sensor response alone or with other sensors to determine the concentration over time of gas or vapor in the vacuum chamber.

BACKGROUND

Vacuum chambers are commonly used in the manufacture of semiconductor wafers. The vacuum chamber provides a controlled environment for the microelectronics circuit manufacturing in which such processes as chemical vapor deposition, aluminum sputtering, plasma etching, or plasma ashing occur. In order for these processes to take place in high yield and with little contamination, the residual gases in the vacuum environment must contain low concentrations of contaminant gases. A typical example of a deleterious gas or vapor in a vacuum environment is water vapor. Great care and effort are used to preclude water from the vacuum environment. Examples of techniques used to this end include baking vacuum chambers at high temperature to remove moisture adsorbed on vacuum chamber walls, vent purging vacuum chambers with inert gases prior to exposure of the chamber to an air environment, minimizing the time of air exposure of the chamber to atmospheric gases, and use of load-lock chambers to pre-treat wafers in a reduced pressure environment prior to their transfer to a high vacuum environment.

Load locks are vacuum chambers which remove the bulk of moisture and other adsorbed gases on substrates by reducing the pressure of the load lock chamber to pressures in the range of 10 to 0.001 torr. The amount of water vapor entering the load lock chamber can vary depending upon the number of wafers placed into the load lock chamber, the time to transfer the wafers into the load lock, the processing history of the wafers, and the concentration of water vapor in the ambient air. Removing the water vapor from the wafers and load lock before transferring the wafers to a central wafer handler or other vacuum chambers for further processes essential for high yields and uniformity of subsequent thin film forming and etching processes.

To prevent wafers with high levels of moisture from entering the central wafer handler, it has been previously proposed to measure the moisture content of the load lock chamber with a capacitive hygrometer sensor mounted to the load lock chamber. This is not desirable since the operation of this sensor relies upon diffusion of the contaminant gas through the chamber to the sensor for detection. While diffusion of gases is fast, the size of the chamber and spacing of substrates within the chamber prevent the gas in the chamber from being well mixed during the short time the chamber is opened. The concentration of a gas or vapor measured by the sensor will not be Indicative of the true concentration or load of gas in the chamber. A sensor located in the chamber may not achieve a zero state after a vacuum cycle since the vacuum level and time may not have been sufficient to remove all the gases or vapors from the chamber. Other sensors which could be suitably mounted to the chamber include a quartz microbalance sensor or a surface acoustic wave sensor.

Capacitive hygrometers and quartz microbalance sensors are commonly used as an equilibrium sensor in a flowing gas stream. In this use the sensor must be at a constant gas pressure. While the sensor output of the equilibrium gas concentration is not dependent upon gas flow, changes in flow will give changes in sensor output until the system is equilibrated.

Residual gas analyzers and other mass spectrometric based gas sensors could be attached to the chamber, however these devices are expensive and require highly trained and dedicated personnel for their use.

U.S. Pat. No. 6,125,687 proposes using a quartz microbalance sensor to detect outgassing of volatile materials placed in a vacuum environment, however, it requires the use of mechanical mixing elements in the chamber, a heat source to enhance outgassing of the material, and cooling elements in proximity to the sensor to enhance detection and condensation of the gas on the sensor. These enhancements are expensive and cumbersome for a semiconductor manufacturing environment. Additionally the presence of a mixing apparatus in the vacuum chamber creates particles which are intolerable for modern semiconductor manufacturing processes.

U.S. Pat. No. 5,170,057 describes an optical method for measuring the moisture content of gases in a reduced pressure environment. The method requires that electromagnetic radiation from a source transverse the chamber to the detector where the change in intensity due to absorption is related to the concentration of moisture in the chamber. Because wafers and wafer handlers are in the chamber, it is difficult to have the electromagnetic radiation transverse the entire chamber thus limiting the positioning of the sensor, the optical path length and ultimately the detection limit of the system. Additionally, ultraviolet light sources are required for moisture detection which requires additional cost of special safety shielding to prevent operator exposure to the radiation source.

In a typical semiconductor manufacturing process, wafers stored in the fabrication area are loaded into the load lock chamber of a wafer manufacturing tool. The load lock chamber is isolated from the vacuum pump by a valve located in a conduit called the fore-line. The fore-line connects the vacuum pump with the chamber and is generally a 1–2 inch diameter pipe for good conductance of gases to the vacuum pump.

In use the load lock is vented from a reduced pressure to atmosphere pressure with a dry inert gas like nitrogen. The load lock chamber is opened and wafers are loaded into the load lock chamber and the chamber is sealed. The valve in the conduit isolating the load lock chamber from the vacuum pump is opened allowing the gas in the load lock to be removed and the pressure in the chamber reduced. When the pressure in the load lock reaches a predetermined level in the range of 0.01 torr to 10 torr, the valve in the conduit between the vacuum pump load lock chamber is closed and wafers are moved from the load lock to the central wafer handler. Wafers are moved by the central wafer handler to different chambers for processing and then returned to the load lock. When all the wafers in the load lock have been processed and returned to it from the central wafer handler, the central wafer handler is isolated from the load lock, the load lock with the processed substrates is vent purged with dry inert gas to atmospheric pressure and the substrates removed from the tool.

During normal operation of a vacuum chamber, the pressure sensor of the vacuum chamber does not provide an indication of an increased water load as measured by a higher than normal base pressure. This is due to the high pumping capacity of modern vacuum pumps and the relatively low partial pressure of gases like water in the chamber. In this case it is possible for wafers with high moisture concentration to be transferred to the central wafer handler. Contamination sensors located in the chamber will only sense gases which are located in the vicinity of the sensor. During chamber evacuation, contamination sensors mounted to or inside the chamber experience a flow of gas away from the sensor and are not capable of measuring the true contaminant gas load of the chamber and substrates as the pressure is reduced. In an optimized vacuum system the contaminant gas load of the vacuum system should be measured in real-time during the pressure reduction step of the vacuum chamber in order to prevent contamination.

What is needed is a method and apparatus for measuring the contaminant load of a vacuum chamber and its contents in real-time. The process and apparatus of the present invention provides a measure of the contamination content of a vacuum chamber during the evacuation process.

SUMMARY OF THE INVENTION

The present invention provides for a gas sensor located in the fore line conduit of a vacuum system and provides for a method of using the output signal from the sensor to determine a measure of the content of a gas species in the vacuum chamber. Such an apparatus and method for determining the content of a gas in a vacuum chamber provides a true measure of the gas content in the chamber in real-time during the evacuation process.

The present invention provides an apparatus for sensing and a method for determining the content and presence of a gaseous contaminant in a vacuum chamber subject to a reduced pressure. Examples of such chambers include a load lock, a central wafer handler, a sputtering chamber or a chemical vapor deposition chamber. Typically the pressure in these chambers range from 0.01 torr to about 650 torr (1.3–86,645 Pascals) depending upon the process. Times for evacuation and exposure of these chambers to a gas range from about 5 seconds to about 5 minutes depending upon the volume and final base pressure of the chamber.

In a first aspect of this invention, a method and sensing apparatus is provided for in the fore-line of a vacuum system to measure the content of gases from the chamber which pass through the fore-line to the vacuum pump. The sensor is isolated from the chamber gas volume by the isolation valve and is at a pressure which substantially reduces the interaction of the contaminant gas or vapor with the sensor. The pressure may be equal to or less than the base pressure of the chamber however it is an advantage to be less than the base pressure of the chamber. When the isolation valve in the fore-line is opened to the chamber, a rapid flow of gas from the chamber into the sensor cavity and to the vacuum pump occurs. The flow of gas from the chamber into the fore-line exposes the sensor to the chamber gases and also causes an interaction of the sensor typical of gas flow or pressure change. Gas flow to the vacuum pump is not constant and the pressure of the system is changing during the initial portion of the evacuation step. An algorithm is used by the sensor apparatus to determine the content of the contaminant gas based upon the sensor response separate from the gas flow and pressure response. An output signal from the sensing apparatus proportional to the concentration of the contaminant gas is determined from the algorithm.

In a second aspect of this invention the output signal from a pressure transducer and the signal from the sensor apparatus are used together to generate an output signal proportional to the concentration of gas or vapor and the pressure of the chamber.

In a third embodiment of this invention the sensor apparatus is used to determine and generate a signal proportional both the concentration and gas pressure of the chamber.

In a fourth embodiment, an additional volume is provided for the sensor housing located downstream from the sensor to further increase the volume of gas and its time in contact with the sensor. The benefit of such an additional volume is additional contact time of the gas with the sensor. During the time when the sensor and the additional volume are isolated from the main vacuum chamber, gas is removed from the sensor housing and added volume. Upon opening of the isolation valve between the chamber and vacuum pump, gas from the chamber flows to fill in the volume of the sensor and the added volume.

In a preferred embodiment, the determination of the sensor state and the calculation of the sensor output is made by difference of the current sensor state with the sensor zero state after a predetermined time or a predetermined pressure is reached.

With respect to uniformity of gas concentration measured by the sensor apparatus of this invention, the location of the sensor in the fore-line provides a mixing of the gas in the chamber as it flows through fore-line to the pump. By locating the sensor in the fore-line both the gas phase concentration of the contaminant and the desorbed concentration of the contaminant from substrates and surfaces in the vacuum chamber can be monitored with time during the pump-down cycle. It is unnecessary to provide mechanical mixing of the gas in the chamber to achieve uniform gas concentration or to measure the all the gas. All the gas is sampled by the sensor using this method.

By locating the sensor in the fore-line of the vacuum system and providing for a method to determine the concentration of gas based upon the transient response of the sensor, fast and reliable measurements proportional to gas concentration can be achieved simply and at low cost. Because the pressure in the fore-line fall below the pressure of the chamber when the isolation valve is closed, the location of the gas sensor in the fore-line provides the advantage of a reference zero gas for the sensor which can be used to simplify the calibration, response, and detection of gaseous contaminants during each processing cycle.

DESCRIPTION OF SPECIFIC EMBODIMENT

The present invention provides an apparatus and a method capable of determining the concentration of gaseous or vapor components in a vacuum chamber during repeated vacuum cycles. While the present invention will be described with reference to a gas composition containing water vapor, it is to be understood that the present invention with be useful for determining the concentration of gases and vapors in general present in a vacuum chamber or vacuum conduits.

Figure 1:
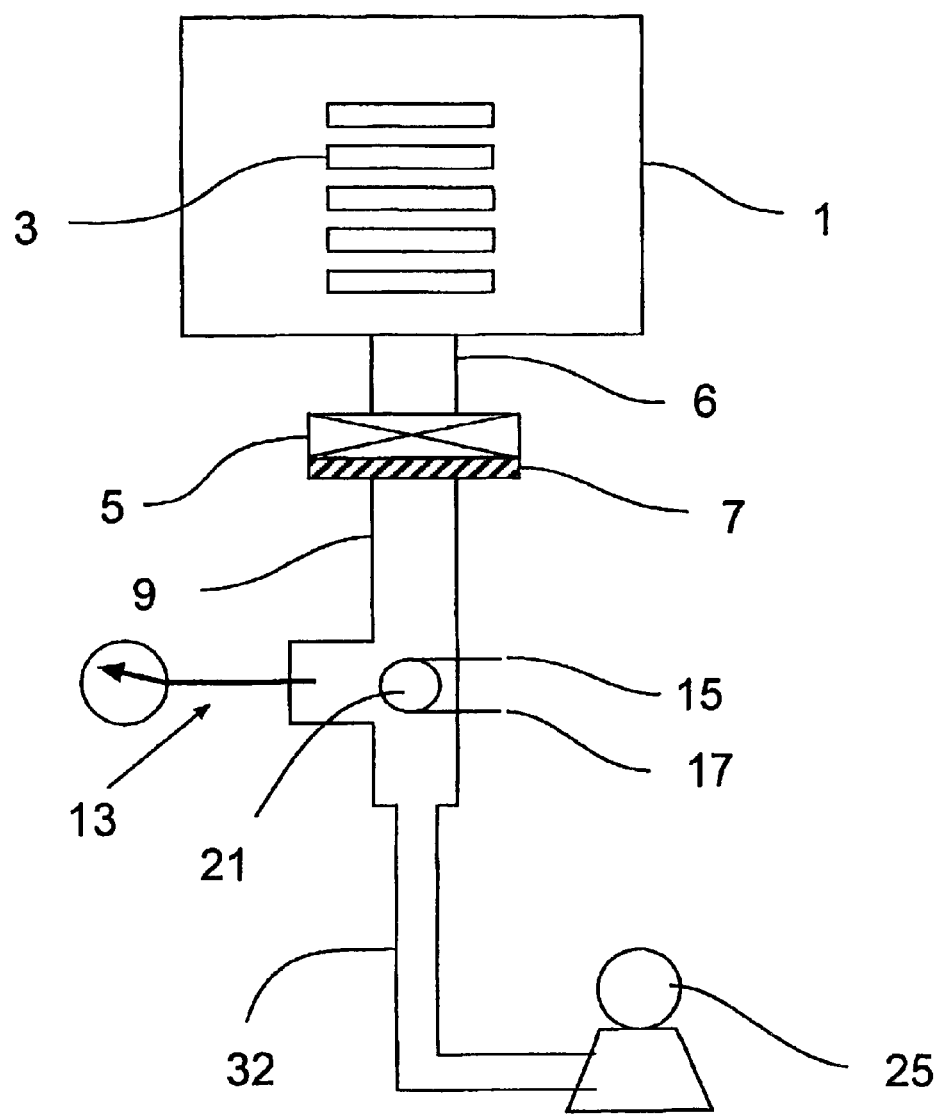
FIG. 1 is a schematic view illustrating the apparatus of this invention.

In the apparatus of this invention illustrated in FIG. 1, the sensor 21 located in the fore-line of a vacuum system and is isolated from the vacuum chamber 1 by an isolation valve 5 located in the fore-line conduit 6 between the vacuum chamber and the fore-line conduit 9 connected to vacuum pump 25. The sensor is placed in the center of the fore-line 9 so that gas passes around the sensor as it flows to the vacuum pump.

Figure 2:
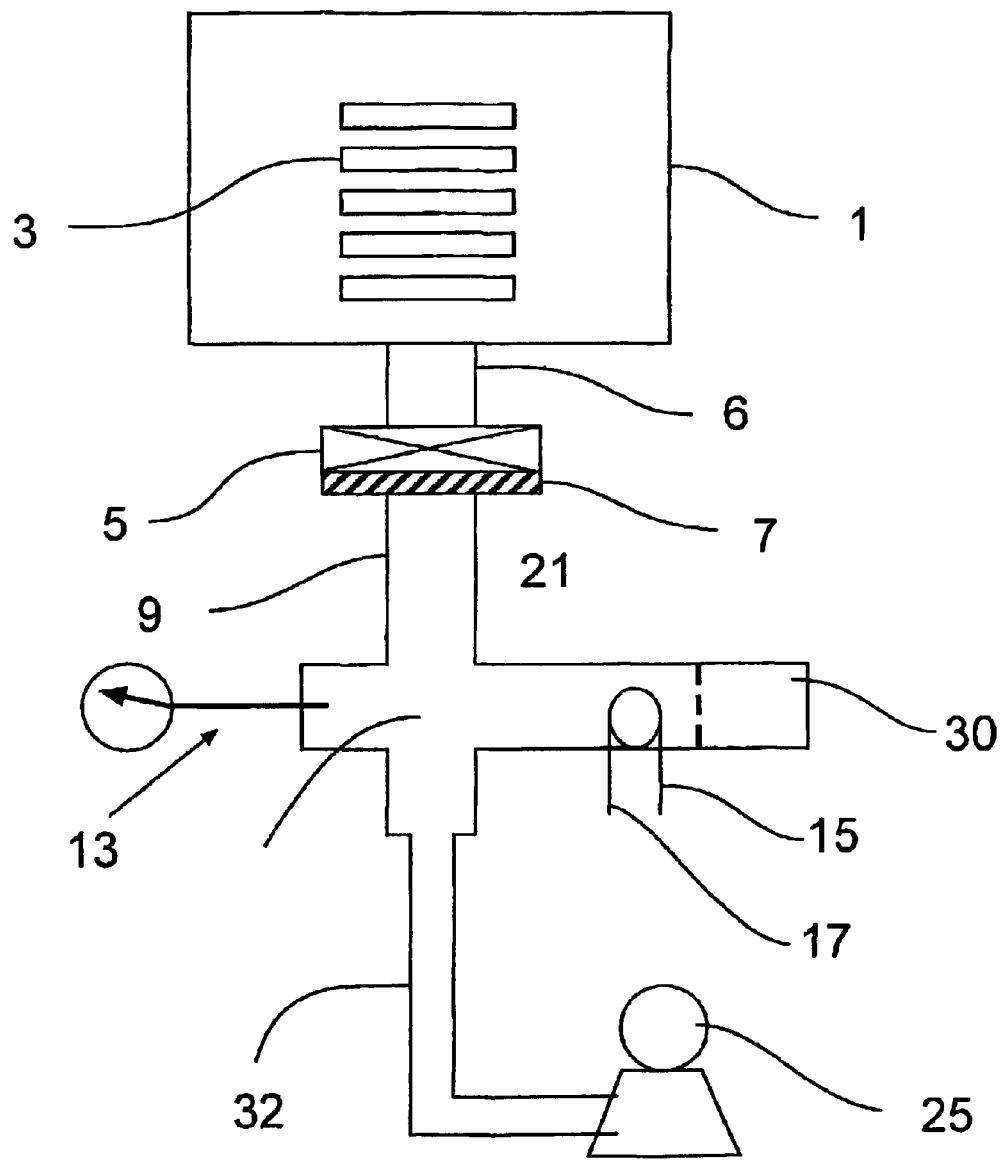
FIG. 2 is another embodiment of the system of this invention using an added volume attached to the sensor.

The sensor can also be placed off center to the fore-line and connected to an additional volume 30 as shown in FIG. 2. The added volume increases the contact time the gas has with the sensor 21.

The sensor can be sealed to the fore-line using standard vacuum o-ring flanges and clamps sold by Varian Vacuum Corporation of Lexington, Mass. Vacuum power feed-through, also from Varian, are useful in mounting the sensor to the vacuum flange and providing for electrical connection of the sensor to a measuring electronics.

One method of detecting the gas or vapor with sensor 21 in the fore-line 9 is by use of a capacitive sensor. Another sensing method useful for detecting moisture and other gaseous vapors in the fore-line is a piezoelectric sensor such as a quartz microbalance sensor or a surface acoustic wave sensor. With suitable coating the sensor will respond to the gas or vapor of interest. For moisture an example of a coating for the sensor 21 is aluminum oxide. A coating useful for detecting tetraethoxysilane vapor in a vacuum chamber is silicon dioxide.

Evacuation of the chamber takes time and depends the initial pressure of the chamber, the volume of the chamber, the speed of the vacuum pump, and the conductance of the vacuum system components. Once the substrates, for example silicon wafers, have been loaded into the vacuum chamber, the isolation valve 5 is opened and the gas from the chamber passes the sensor 21 as it flows to the vacuum pump 25 through conduit 6 and conduit 9.

When utilizing a vacuum chamber for microelectronics manufacturing the pressure is reduced to sub-atmospheric pressure between about 650 and about 0.01 torr (86,582 and about 1.33 Pascals), preferably between about 60 and 0.01 ton (7,992 and about 1.33 Pascals).

Referring to FIG. 1, the system of this invention is illustrated. A sensor 21 is mounted in fore-line 9 connected to vacuum pump 25 by conduit 32. A gate valve 5 and throttle valve 7 are placed between sensor 21 and vacuum chamber 1. The valve 5 is connected to vacuum chamber 1 through fore-line conduit 6. Electrical leads for excitation and output from the sensor are provide through lead 15 and lead 17 and are connected electrical device not shown.

Fore-line conduit 9 is connected to a vacuum source 25 through conduit 32. When valve 5 is closed the vacuum source effects a sub-atmospheric pressure in conduit 9 on sensor 21 which removes gases and vapors interacting with sensor 21 in conduit 9. The pressure on sensor 21 in conduit 9 when valve 5 is closed is equal to and preferably less than the final pressure of the vacuum chamber when valve 5 is opened and the chamber 1 is evacuated. The preferred pressure in conduit 9 is in the range of 1 to 0.001 torr.

After removal of gases from the conduit 9 for a predetermined time, a predetermined sensor output, or to a predetermined pressure, and before the valve 5 is opened, the output signal from the sensor 21 is determined. The sensor signal output in this condition of pressure and time is called the zero state signal. When valve 5 is closed, the pressure of the conduit is less than when valve 5 is open and the chamber being evacuated. As such, the partial pressure of the target gas in the conduit with valve 5 closed is less than it is in the conduit with valve 5 opened to the chamber 1. The lower partial pressure of the gas in the conduit with the valve closed provides a zero point for the sensor. The zero state reference signal for the sensor is used in the algorithm for determining the gas or vapor concentration in the chamber. Pressure in the conduit 9 is measured by pressure gauge 13.

During the pressure reduction of conduit 9, wafers or other substrates, 3, in FIG. 1 to be processed are loaded into the chamber 1 through an opening in the chamber not shows Chamber 1 will have been purged from a previous vacuum cycle with a source of dry inert gas like argon, nitrogen or helium. The inert gas source is not shown.

After substrates 3 have been loaded into chamber 9 and the opening in the chamber closed, isolation valve 5 is opened and gases and vapors from the chamber and substrates are removed through conduit 6, past sensor 21 in conduit 9 and to the vacuum pump 25.

Once the isolation valve 5 is opened, the sensor 21 and pressure gauge 13 interact with the gas and vapors in the chamber as they are removed from the system through the conduit 32. After a predetermined time, a predetermined pressure difference, or a predetermined rate of change of sensor response, the output signal of the sensor is measured and used in an algorithm for determining the concentration of the gas. The signal from the sensor after one of these conditions is met is referred to as the current sensor state.

An algorithm programmed into the microprocessor used to operate the sensor is used to determine the measure of gas or vapor concentration in the vacuum chamber from the response of the sensor during the evacuation cycle. The algorithm uses input signals from the gas sensor, pressure transducer, and sensor microprocessor clock to calculate the gas concentration in the vacuum conduit.

In a first step the algorithm determines the pressure of the conduit and time the valve in the conduit has been opened to the vacuum source. When the value of the pressure or time exceeds a predetermined threshold value, the algorithm in a second step recalculates the difference between the output signal from the current state of the sensor 21 exposed to the gas and the reference zero state of the sensor when it was isolated from the vacuum chamber. The calculation of the difference in output signal from the sensor and the reference state of the sensor is repeated for each sensor reading received by the microprocessor until a second predetermined threshold value of the pressure or time is exceeded. The second predetermined threshold value for the pressure or time indicates the end of the vacuum chamber evacuation.

The signal difference of the sensor in the two states as determined by the microprocessor is proportional to the concentration of the gas or vapor removed from the chamber during the evacuation cycle. In a third step the algorithm programmed into the microprocessor takes the signal difference between the zero state and the current sensor state and inputs it as an argument it into a pre-determined response equation for the sensor. The response equation output is a displayed as a numeric value proportional to the concentration of the gas or vapor present in the chamber. The concentration can be reported as a partial pressure, mass or volume fraction.

A pre-determined response equation for the sensor is obtained in a separate step by exposing the sensor to known partial pressures of the gas to be detected and recording the sensor response to the different gas partial pressures. A function fitting program, for example Excel ®. by Microsoft Corporation, is used to derive an equation relating the sensor response to the partial gas pressure.

The content or measure of gas or vapor in the system is output as a function of time through a display device. An examples of such a display device is an LR 300 from Millipore Corporation, Bedford, Mass. Alternatively, the output from the sensor can be received by a computer through its serial port and displayed on the computer screen as a digital or graphical output.

When the pressure in the conduit 9 or in the chamber 1 reaches a predetermined level, the sensor output has reached a predetermined rate of change, or the system has been evacuated for a predetermined time interval, the valve 5 is closed. Pressure in the conduit 9 is reduced to the range 1 to 0.001 torr and the substrates in chamber 1 are processed in other chambers connected to chamber 1 not shown.

After the substrates in the chamber have been processed and returned to chamber 1, the chamber is filled with a dry inert gas and the substrates removed. Once the substrates have been removed, new substrates are placed in the chamber and the vacuum cycle initiated after the zero sensor output signal is determined.

The following example illustrates the present invention and is not intended to limit the same.

EXAMPLE 1

Figure 3:
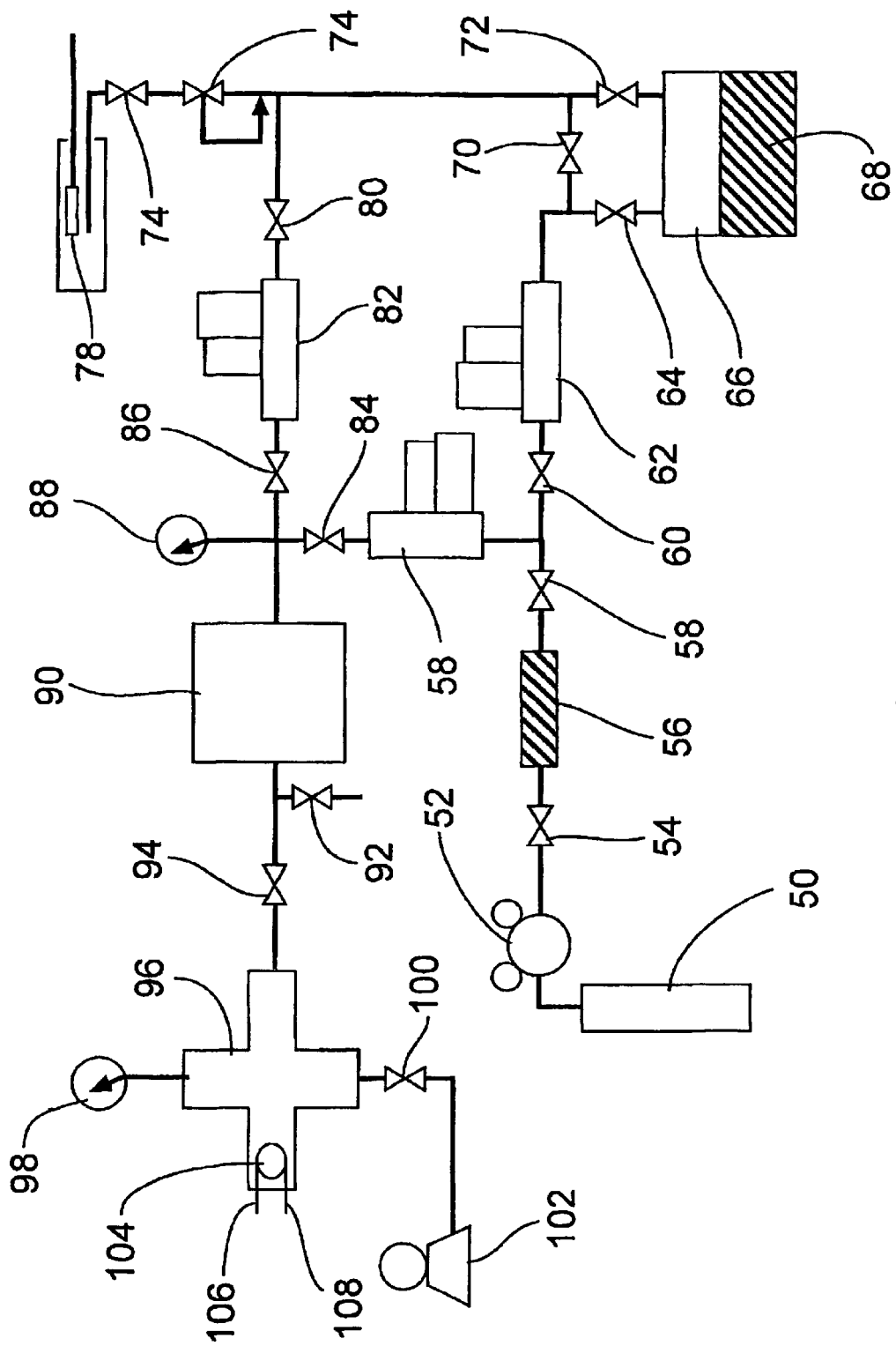
FIG. 3 is a schematic diagram of a test manifold utilized in Example 1.

A test manifold, FIG. 3, was designed to illustrate the method and apparatus for the detection of moisture in a vacuum chamber. The manifold was designed to deliver prepared challenges of moisture into a vacuum chamber to simulate exposure of the chamber to atmospheric gases.

An 8 liter vessel, 90, fit with vacuum flanges was connected to isolation valve, 94, vent valve 92, and connected to a vacuum cross 96, from Varian Vacuum Corporation, Lexington, Mass. In the vacuum cross was mounted a 10 MHz aluminum quartz microbalance crystal from International Crystal, Oklahoma City, Okla. The crystal was mounted on the leads from a power vacuum feedthrough from Varian Vacuum, and connected by leads 106 and 108 to an oscillator circuit, not shown, from Millipore Corporation, Bedford, Mass. Also mounted in the vacuum cross was Pirani vacuum gauge, 98, from BOC Edwards, Murry Hill, N.J. The vacuum cross was connected to vacuum pump 102 by valve 100. The crystal was coated with a hygroscopic organic sulfonic acid.

Challenges for the vacuum chamber 90 were generated by flowing bottled nitrogen 50 through a gas purifier 56, Waferpure®, Millipore Corporation, through mass flow controller 62 and through vessel 66 containing water 68. The concentration of the moisture vapor generated was measured by relative humidity sensor, Omega, Stanford, Conn. The moisture challenge was delivered to chamber 90 through mass flow controller 82.

In a typical cycle isolation valve 94 was closed and the pressure in 96 reduced to about 0.01 torr. Simultaneously, valve 84 was opened and dry nitrogen through mass flow controller, Unit Instruments, Yorba Linda, Calif., passed into chamber 90 until the pressure in 90 measured by pressure gauge 88 was 101,325 Pascals. Valve 84 was closed and the gas from mass flow controller 82 flowed into the chamber 90 with valve 92 and valve 80 opened for 1 minute. Blank samples of gas without moisture were prepared by closing valves 64 and 72 and opening valve 70.

After 1 minute exposure of the 8 liter chamber to wet or dry gas flow for 1 minute, valve 92 was closed, valve 80 was closed and valve 94 opened. The chamber 90 was evacuated until a pressure of 1 torr was reached as measured by pressure sensor 98.

The frequency change of the sensor 104 was logged on an IBM compatible 486 SX computer from Gateway Corporation through as RS-232 connection to the serial port on the computer. Data from the sensor was taken at a rate of two points each second.

The challenges delivered to the chamber were dry nitrogen, 15 percent relative humidity at 21 degrees Celsius, 23 percent relative humidity at 21 degrees Celsius, and 37 percent relative humidity at 21 degrees Celsius. The sensor response to each of these conditions versus time is illustrated in the curves labeled 132, 130, 128, and 126 respectively shown in FIG. 4.

For the purposes of example the response of the sensor, as shown graphically by 130 in FIG. 4, will be described in detail. Curve 130 shows the response of the sensor to 15 percent relative humidity at 21 degrees Celsius as the chamber is evacuated through the conduit 96 in FIG. 3. The absolute value of the difference of the sensor frequency in the current state subtracted from the sensor reference frequency in the zero state is shown on the y-axis, the time that the valve 94 has been opened is shown on the x-axis.

The zero state frequency of the sensor was 8829.082 Hz. At 1 second after the valve 94 was opened the current sensor state signal was 8838.135 Hz, at 2.5 seconds the current state signal was 8830.921 hertz, at 18.5 seconds the current sensor state signal was 8834.481 hertz, and at 90 seconds the current sensor state signal was 8831.146 hertz. Other current sensor state valves were recorded by the computer during the test.

Figure 4:
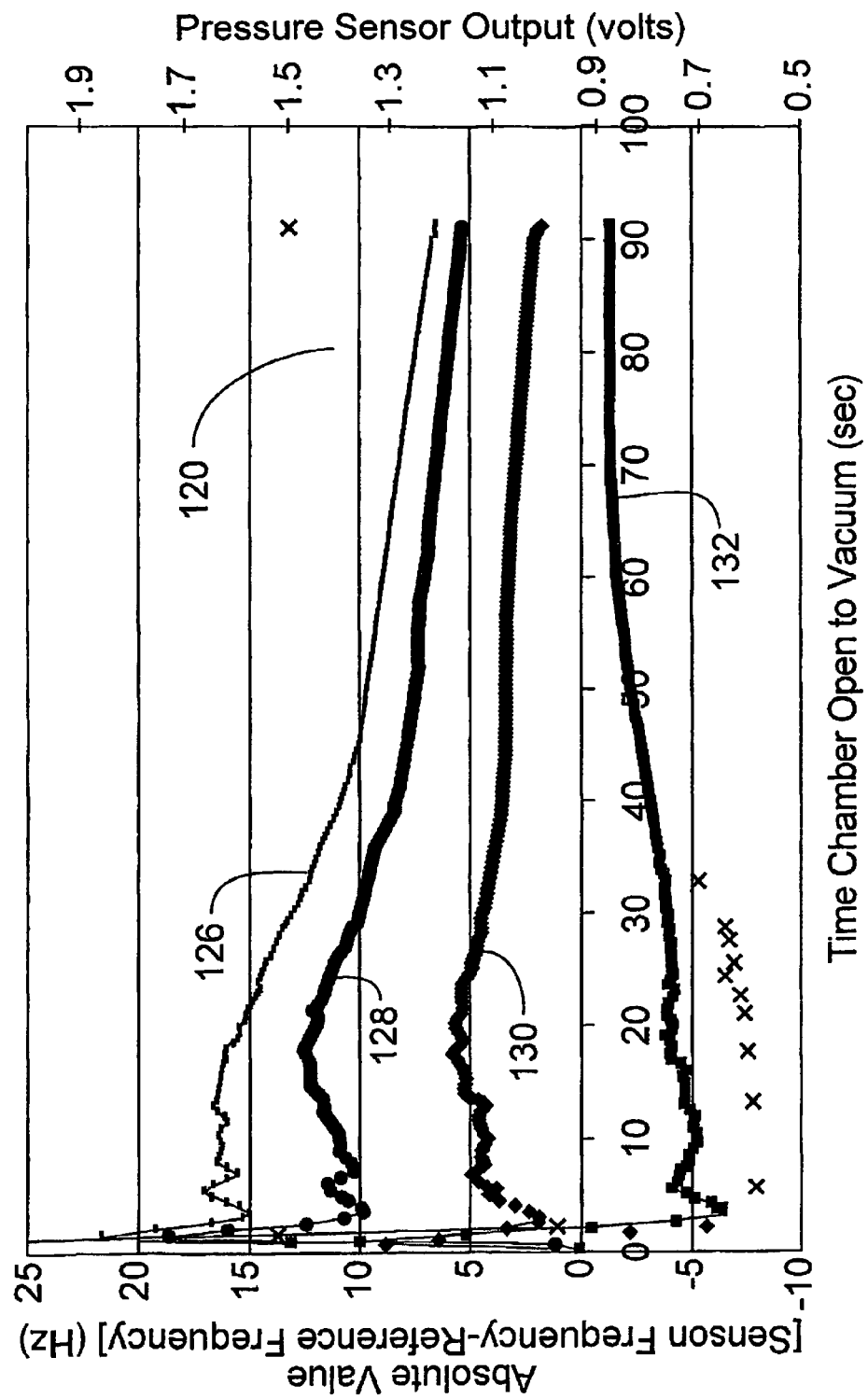
FIG. 4 is a graph illustrating the response of the sensor to different concentrations of moisture in Example 1 with the apparatus of this invention.

For sensor response 130 in FIG. 4 from time zero to one second, the difference of the sensor in the current state minus the sensor in the zero state rises rapidly to 9.3 hertz, the difference between 8838.135 hertz and the zero state signal of 8829.082 hertz. The difference then decreases to 1.8 hertz at 2.5 seconds. From 2.5 seconds to 18.5 seconds the difference between the zero state of the sensor and the current state of the sensor increased to 5.6 hertz due to adsorption of moisture in the chamber on the sensor surface. From 18.5 seconds to 90 seconds the moisture from the chamber adsorbing onto the sensor decreased until the difference of the sensor in the current state minus the sensor in the zero state was 2.06 hertz.

The response of the pressure sensor 98 to the evacuation of vacuum cross 96 for each of three different moisture challenges and the zero gas delivered to the chamber 90 is shown as the curve labeled 120 in FIG. 4. The curve 120 consists of four identical curves superimposed on top of each other. The response of the pressure sensor with time as depicted in 120 is unchanged over the course of the four different relative humidity challenges. This illustrates the inability of pressure sensors to determine vapor concentration in the system.

The partial pressure of moisture for each of the conditions, 126. 128, 130, and 132 shown in FIG. 4, were calculated using a pre-determined response equation, (1), for the sensor.

$$\left(\frac{(\text{abs}(\text{sensor current state response} - \text{sensor zero state response}))}{154.32}\right)^{\left(\frac{1}{0.592}\right)} \quad (1)$$

As an example, the difference of the current state at 18.5 seconds signal minus the zero state signal for the 15 percent relative humidity condition was 5.38 hertz. This value input into equation (1) returns a value of 0.0034 torr. This value is shown in 144 In FIG. 5 at the time 18.5 seconds.

Figure 5:
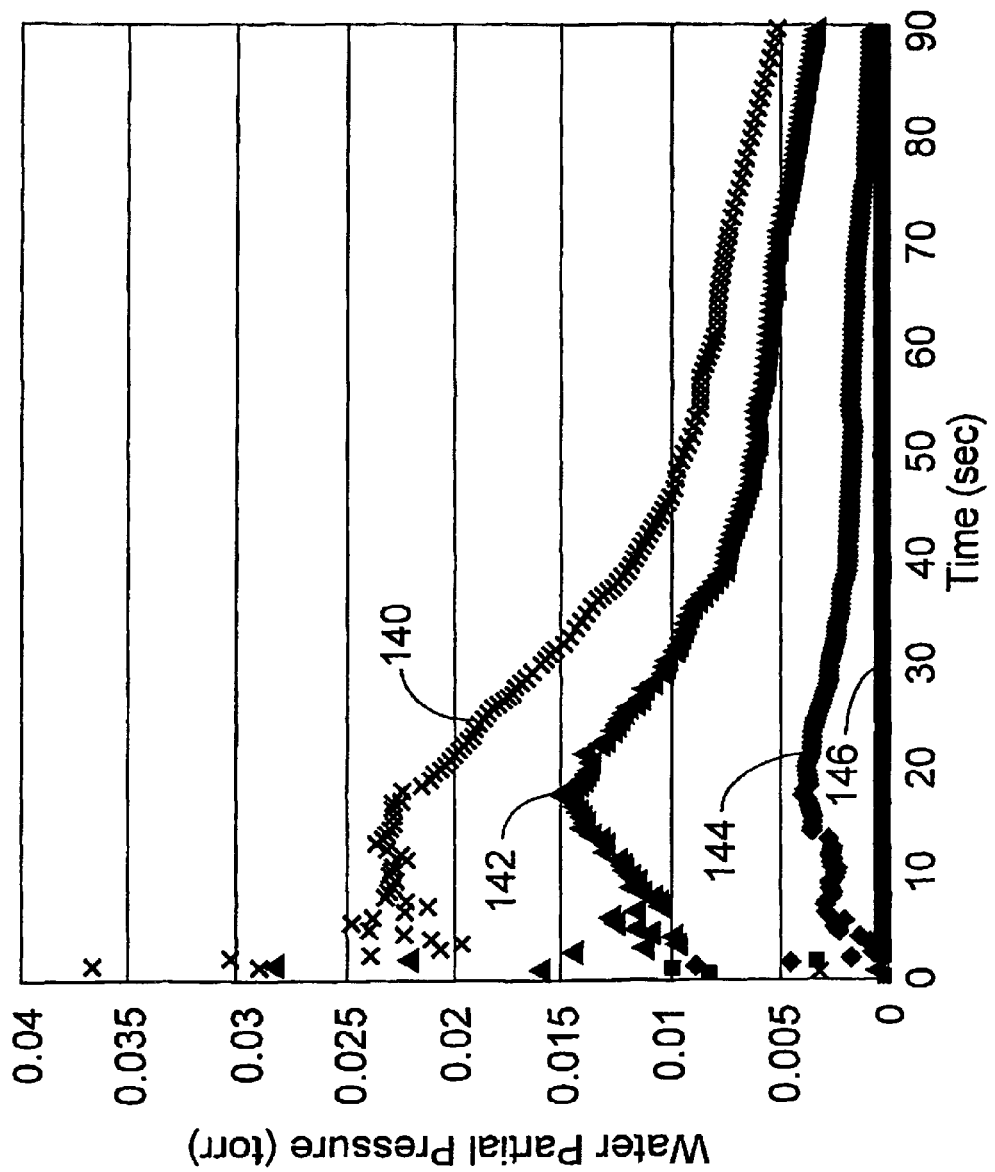
FIG. 5 is a graph of partial pressure of moisture versus time illustrating the output of the sensor utilized in Example 1 with the apparatus and method of this invention.

The application of the algorithm to the sensor response for each of the conditions in FIG. 4 is shown graphically in FIG. 5. Curves labeled 140, 142, 144, and 146 refer to the calculated partial pressure of water calculated from the response of the sensor to the moisture in the chamber during the pump down for 37% relative humidity, 23% relative humidity, 15% relative humidity, and 0% relative humidity respectively. For purposes of this example, differences in frequency between the sensor and the zero reference state of the sensor were assigned a value of zero partial pressure.

What is claimed is:

1. A method for measuring the concentration of a gas in a vacuum environment the process comprising:

creating a zero state for a gas sensor isolated from a vacuum chamber;

determining the sensor output signal for the zero state;

reducing the pressure in the vacuum chamber and exposing said sensor to a flow of gas from said vacuum chamber having reduced pressure to generate a current sensor state;

determing a sensor output signal for the current sensor state;

computing the difference between the zero state and the current sensor state output signals to create a raw data signal; and applying the raw data signal to a predetermined response equation to generate an output signal proportional to the concentration of the gas evacuated from the chamber wherein the calculated output signal is proportional to the rate of change of the difference between the sensor's current state and the sensor's zero state.

2. An apparatus for measuring the gas content of a vacuum chamber, the apparatus comprising:

a gas sensor configured to interact with a gas being removed from the vacuum chamber to be measured, wherein the gas sensor has substantially the same coating composition as the substrates present in the vacuum chamber; and a microprocessor, said microprocessor configured to compute an output signal from zero state and current sensor state signals with a pre-determined response equation, wherein said output signal can be used to measure the concentration of the vacuum chamber gas.

3. An apparatus for measuring the gas content of a vacuum chamber, the apparatus comprising:

a valve having an inlet and an outlet;

the inlet of said valve connected to and in gas fluid communication with said vacuum chamber;

a capacitive hygrometer gas sensor sealed to a conduit and configured to interact with a gas being removed from the vacuum chamber flowing through the conduit, said conduit further comprising an inlet and an outlet, the inlet of said conduit connected to and in gas fluid communication with the outlet of said valve;

a source of vacuum for removing gas from said vacuum chamber, said source of vacuum connected to and in gas fluid communication with the outlet of said conduit; and a microprocessor, said microprocessor configured to compute an output signal from zero state and current sensor state signals with a pre-determined response equation, wherein said output signal can be used to measure the concentration of the vacuum chamber gas.

4. An apparatus for measuring the gas content of a vacuum chamber, the apparatus comprising:

a gas sensor configured to interact with a gas being removed from the vacuum chamber to be measured, wherein the sensor has substantially the same coating composition as the walls of the vacuum chamber; and a microprocessor, said microprocessor configured to compute an output signal from zero state and current sensor state signals with a pre-determined response equation, wherein said output signal can be used to measure the concentration of the vacuum chamber gas.

5. The apparatus of claim 3 wherein the sensor coating has substantially the same composition as the substrates present in the vacuum chamber.

6. The apparatus of claim 3 wherein the sensor coating has substantially the same composition as the walls of the vacuum chamber.

* * * * *